Nov. 19, 1963 H. B. LEWIS ETAL Plant Pat. 2,306
AZALEA PLANT
Filed Sept. 7, 1962 2 Sheets-Sheet 1
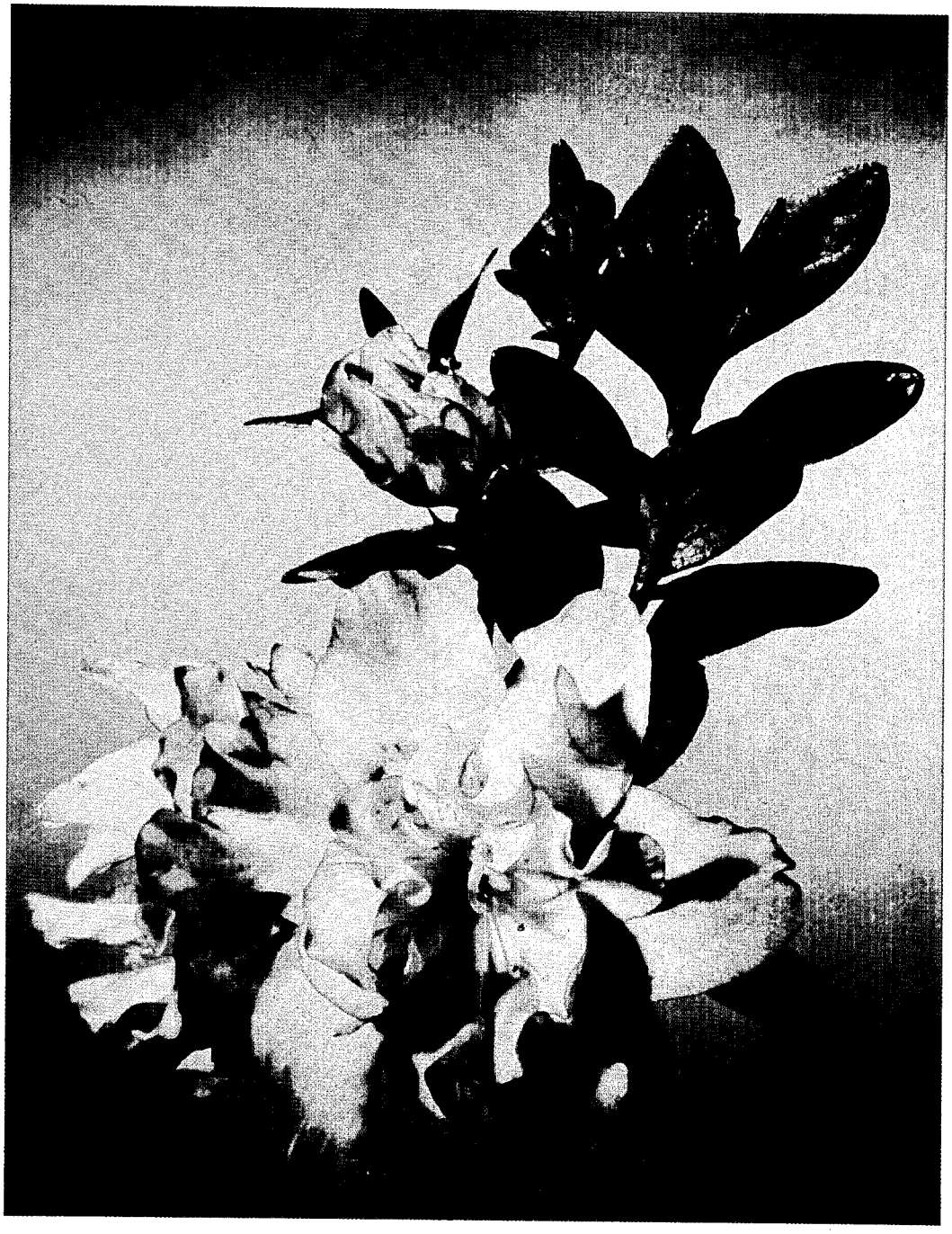
Inventors
H. B. Lewis and
H. H. Lewis
By: Robb & Robb
Attorneys AZALEA PLANT
Filed Sept. 7, 1962 2 Sheets-Sheet 2
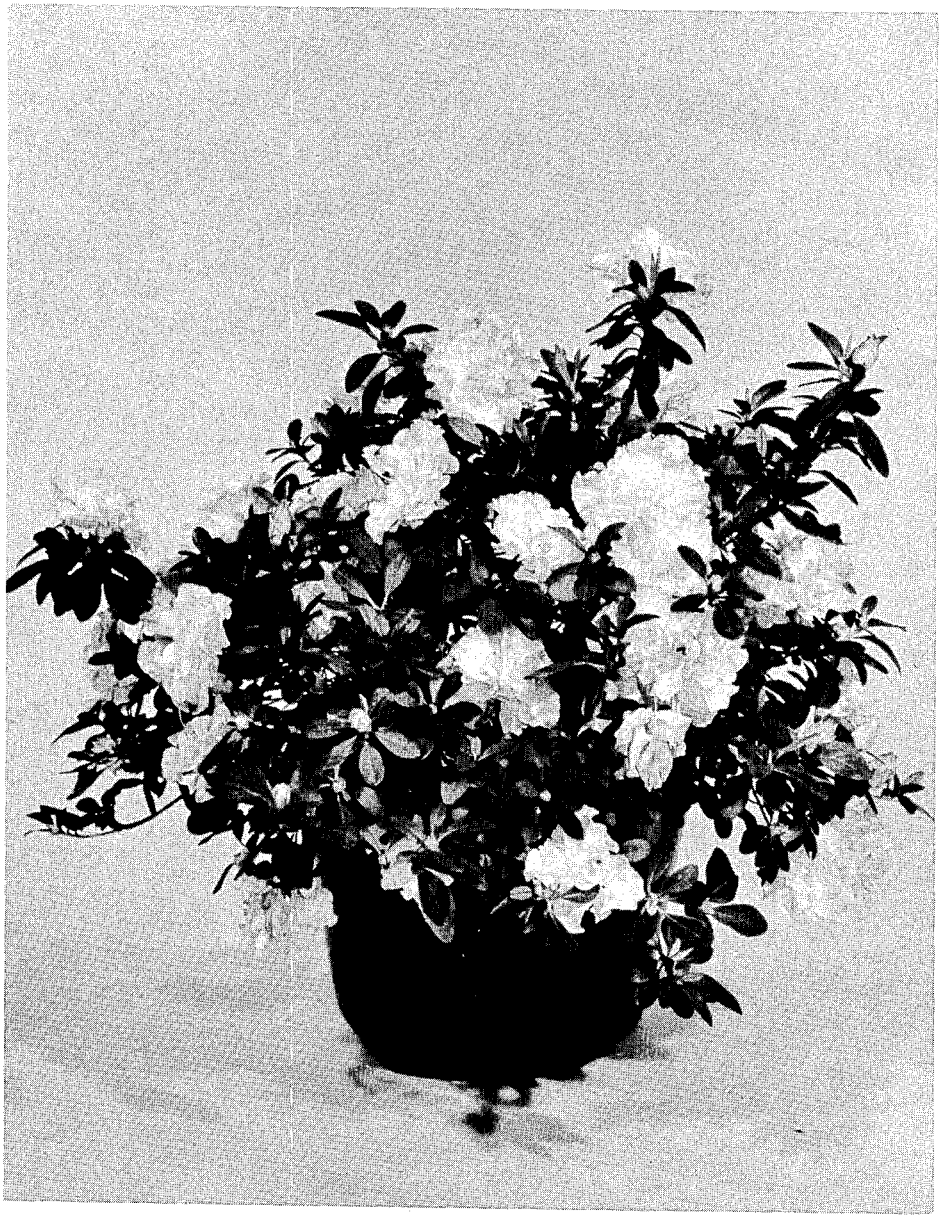
Inventors.
H. B. Lewis and
H. H. Lewis
By: Robb & Robb
Attorneys.

United States Patent Office

Plant Pat. 2,306
Patented Nov. 19, 1963

2,306
AZALEA PLANT

Hubert B. Lewis and Helen H. Lewis, both of 16562 E. Leffingwell Road, Whittier, Calif.

Filed Sept. 7, 1962, Ser. No. 222,248
1 Claim. (Cl. Plt.—55)

The present invention relates to a new and distinct variety of azalea plant which was originated by us by crossing the Belgian Indian variety known as "Brillanta Belgica" (unpatented) with the variety known as "Mme. Pericat" (unpatented), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) A vigorous habit of growth;

(2) A flower form in which the center of the flower is raised and is double or semi-double; and (3) A distinctive and attractive general color tonality of the flowers ranging in shade from dark to light vermilion.

Our new azalea variety does not resemble either parent with respect to either its foliage or its flowers, but has inherited a vigorous habit of growth from its pollen parent. The unusual and distinctive color of its flowers primarily makes it most outstanding and differentiates the new variety from all other azaleas of which we are aware.

A sexual reproduction of our new variety but cuttings, as performed at Rivera, California, and at Whittier, California, shows that the foregoing characteristics and distinctions come true to form and are established and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Much-branched.
Habit: Vigorous; strong; branching; compact.
Rooting habit: Good; roots easily.
Foliage:
*Size.*—Medium.
*Quantity.*—Abundant.

*Color.*—New foliage: upper side—Spinach Green, Plate 0960; under side—Scheeles Green, Plate 860/1. Old foliage: upper side—Parsley Green, Plate 00962; under side—Spinach Green, Plate 0960/1.
*Shape.*—Oval.
*Texture.*—Upper side—semi-glossy; smooth. Under side—smooth; veined.
*Margin.*—Smooth.
*Aspect.*—Good.
*Disease resistance.*—Very good resistance to ordinary diseases to which azalea plants are normally subject, as determined by comparison with other varieties grown under the same cultural conditions at Whittier, California.

*Flowers*

Borne: 2 or 3 to stem; on short, strong stems.
Blooming habit: Heavy.
Blooming season: Normally in late spring, but with early pruning, can be brought into bloom earlier; very good suitability for forcing.
Quantity of bloom: Free, both outdoors and in greenhouse.
Petalage: Normally has 5 petals in each hose, but offset and having tufted center.
*Color.*—Very narrow outer edge of Vermilion, Plate 18/1, shading to Scarlet, Plate 19/2 toward center, and shading from Germanium Lake, Plate 20/3 to White from center to throat, with 2 upper petals of each hose near throat being dotted with Phlox Pink, Plate 625/1.
*Texture.*—Firm.
*Appearance.*—Outstanding color; flowers have raised double or semi-double center, with outer petals being quite wavy and almost ruffled, with 2 upper petals of each hose being dotted.
*Shape.*—Semi-double hose in hose.
*Arrangement.*—Inner hose offset from outer hose and having raised tufted center.
Bud: Color—Carmine Rose, Plate 621.

*Reproductive Organs*

Stamens: 5 in number; mostly attached to center petals. Color—yellow.
Pollen: Fairly free.
Styles: Well developed.
Ovaries: Normal.

We claim:

A new and distinct variety of azalea plant, substantially as herein shown and described, characterized particularly as to novelty by the unique combination of a vigorous habit of growth, a flower form in which the center of the flower is raised and is double or semi-double, and a distinctive and attractive general color tonality of the flowers shading from dark to light vermilion.

No references cited.